United States Patent [19]
Mertens et al.

[11] Patent Number: 5,952,464
[45] Date of Patent: Sep. 14, 1999

[54] LABELLED PEPTIDE COMPOUNDS

[75] Inventors: John Mertens; Dirk Tourwe; Marc Ceusters, all of Brussels, Belgium

[73] Assignee: Mallinckrodt Inc., St. Louis, Mo.

[21] Appl. No.: 08/737,299

[22] PCT Filed: Feb. 21, 1995

[86] PCT No.: PCT/US95/02131

§ 371 Date: Jul. 21, 1997

§ 102(e) Date: Jul. 21, 1997

[87] PCT Pub. No.: WO95/22341

PCT Pub. Date: Aug. 24, 1995

[30] Foreign Application Priority Data

Feb. 18, 1994 [EP] European Pat. Off. ............ 94200409

[51] Int. Cl.$^6$ .......................... A61K 38/04; A61K 38/00; A61K 51/00

[52] U.S. Cl. ..................... 530/329; 530/323; 530/327; 514/14; 514/16; 424/1.69

[58] Field of Search ................. 514/16, 17, 14, 514/13, 15; 530/329, 327, 323; 424/1.11, 1.57, 1.69, 9.1, 9.3, 9.34, 9.341, 9.4, 9.411, 9.6; 435/9.75, 7.23

*Primary Examiner*—Paula K. Hutzell
*Assistant Examiner*—Timothy A. Worrall

[57] ABSTRACT

The invention relates to a labelled peptide compound, wherein the peptide has a selective neurotensin receptor affinity and is represented by the general formula $$R_1\text{-}(^1Pro)_n\text{-}^2Xaa\text{-}^3Xbb\text{-}^4Xcc\text{-}^5Xdd\text{-}^6Xee\text{-}^7Leu\text{-}OH \text{ (SEQ ID NO:2)} \quad (I)$$

wherein:

$R_1$ is a $(C_1\text{-}C_3)$alkanoyl group, an arylcarbonyl group, an aryl-$(C_1\text{-}C_3)$alkanoyl group, or a chelating group attached by an amide bond or through a spacing group to the peptide molecule;

Xaa and Xbb are each individually Arg or Lys;

Xcc is an unsubstituted or substituted cyclic amino acid, preferably selected from Pro and Hyp;

Xdd is Tyr, Trp or Phe;

Xee is Leu, Ile or t.-butylalanine; and n is 0 or 1;

and wherein said peptide is labelled with (a) a metal isotope, or (b) with a radioactive halogen isotope; on the understanding that:

(i) if the label is a metal isotope, $R_1$ represents a chelating group for chelating said isotope; and (ii) if the label is a radioactive halogen isotope, said halogen isotope is attached to $^4$Tyr in the 2-position of the phenyl ring, to $^4$Trp, or to the aryl group of substituent $R_1$.

10 Claims, No Drawings

LABELLED PEPTIDE COMPOUNDS

The present invention relates to labelled peptide compounds, to a method of preparing these compounds, to a pharmaceutical composition comprising these compounds, to the use of this composition for diagnosis and therapy, and to a kit for preparing a radiopharmaceutical composition.

Neurotensin is a thirteen amino acid peptide, in 1973 isolated from bovine hypothalamus. It has the following structure:

pGlu-Leu-Tyr-Glu-Asn-Lys-Pro-Arg-Arg-Pro-Tyr-Ile-Leu-OH (SEQ ID NO:1:)

High concentrations of neurotensin are found in discrete regions of the mammalian central nervous system. In addition, neurotensin interacts with specific receptors in the periphery. During the last decade, neurotensin receptors were found in several tumour cells, like small cell lung carcinoma, human colon carcinoma and human meningiomas.

Two radioiodinated neurotensin derivatives are mentioned in the literature. Because of the existence of two tyrosine residues in the neurotensin sequence, iodination of neurotensin yields a complex mixture of radioiodinated peptides, that possess very different biological properties and, moreover, are difficult to purify. Therefore, Mazella et al. (J. Biol. Chem. 1983, 258, 3476–3481) synthesized a neurotensin analogue in which the tyrosine-11 is replaced by a tryptophan residue: [Trp$^{11}$]neurotensin. Iodination (with 125-iodide under electrophilic conditions on the aromatic ring of tyrosine-3) results in a mono-iodo derivative showing a $K_d$ of 0.1 nM for binding on rat brain synaptic membranes. Preliminary experiments from the same group of researchers (Sadoul et al.; Biochem. Biophys. Res. Commun. 1984, 120, 812–819) indicated that neurotensin receptors in human brain showed a low affinity for monoiodo-[Trp$^{11}$]-neurotensin, making this compound unsuitable for binding experiments. The same group of researchers succeeded later on in preparing a mono-iodo derivative of neurotensin itself; only tyrosine-3 was iodinated with 125-iodide in this method. This radioiodinated analogue has a $K_d$ of 0.2 nM for binding on rat brain synaptic membranes and a $K_d$ of 0.26 nM for binding to human brain neurotensin receptors.

The labelled natural neurotensin as well as the labelled tryptophan11 neurotensin analogue, however, suffers from an enzymatic breakdown due to cleavage of peptide bonds, resulting in an in vivo half-life of only a few minutes.

Structure-activity studies (Granier et al.; Eur. J. Biochem. 1982, 124, 117–125) revealed that the right-hand part of the neurotensin molecule fulfills the structural requirements for mimicking the entire sequence, provided its α-amino end group is protected by acetylation. The binding affinities of this analogue are comparable with those of neurotensin in two binding assays, viz. the binding assay on rat brain synaptic membranes and that on HT 29 cells.

This analogue contains one remaining tyrosine residue which can be readily radioiodinated using electrophilic substitution of the hydrogen in the ortho position of the phenolic group. Structure-activity studies revealed, however, that iodination in the 3-position of said tyrosine residue of this analogue results in a remarkable loss of receptor affinity, viz. with a factor of 20 (Mazella et al.; see above).

It is the objective of the present invention to provide a labelled peptide compound which has a selective affinity to neurotensin receptors, comparable with that of neurotensin itself, and which has a sufficient enzymatic resistance to allow its use in diagnosis and therapy.

This objective can be achieved by a labelled peptide compound, wherein the peptide has a selective neurotensin receptor affinity and is represented by the general formula

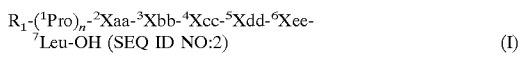

$R_1$-($^1$Pro)$_n$-$^2$Xaa-$^3$Xbb-$^4$Xcc-$^5$Xdd-$^6$Xee-$^7$Leu-OH (SEQ ID NO:2)  (I)

wherein:

$R_1$ is a ($C_1$–$C_3$)alkanoyl group, an arylcarbonyl group, an aryl-($C_1$–$C_3$)alkanoyl group, or a chelating group attached by an amide bond or through a spacing group to the peptide molecule;

Xaa and Xbb are each individually Arg or Lys;

Xcc is an unsubstituted or substituted cyclic amino acid, preferably selected from Pro and Hyp;

Xdd is Tyr, Trp or Phe;

Xee is Leu, Ile or t.-butylalanine; and n is 0 or 1;

and wherein said peptide is labelled with (a) a metal isotope selected from the group consisting of $^{99m}$Tc, $^{203}$Pb, $^{67}$Ga, $^{68}$Ga, $^{72}$As, $^{111}$In, $^{113m}$In, $^{97}$Ru, $^{62}$Cu, $^{64}$Cu, $^{52}$Fe, $^{52m}$Mn, $^{51}$Cr, $^{186}$Re, $^{188}$Re, $^{77}$As, $^{90}$Y, $^{67}$Cu, $^{169}$Er, $^{121}$Sn, $^{127}$Te, $^{142}$Pr, $^{143}$Pr, $^{198}$Au, $^{199}$Au, $^{161}$Tb, $^{109}$Pd, $^{165}$Dy, $^{149}$Pm, $^{151}$Pm, $^{153}$Sm, $^{157}$Gd, $^{159}$Gd, $^{166}$Ho, $^{172}$Tm, $^{169}$Yb, $^{175}$Yb, $^{177}$Lu, $^{105}$Rh and $^{111}$Ag, or (b) with a radioactive halogen isotope; on the understanding that:

(i) if the label is a metal isotope, $R_1$ represents a chelating group for chelating said isotope; and (ii) if the label is a radioactive halogen isotope, said halogen isotope is attached to $^4$Tyr in the 2-position of the phenyl ring, to $^4$Trp, or to the aryl group of substituent $R_1$.

Suitable examples of aryl groups in $R_1$ are: phenyl, halo-substituted phenyl or indolyl; preferably phenyl, 4-fluorophenyl, 2- or 4-bromophenyl, 2-iodophenyl, 4-fluoro-2-bromophenyl and 4-fluoro-2-iodophenyl. Suitable examples of radioactive halogen isotopes are: $^{123}$I, $^{124}$I, $^{125}$I, $^{131}$I, $^{75}$Br, $^{76}$r, $^{77}$Br and $^{82}$Br.

In the above labelled peptide compounds one or more of the amino acids may have the D-configuration instead of the normal L-configuration. The labelled peptide compounds of the invention may also comprise so-called pseudo peptide bonds, viz. —CH$_2$—NH— bonds, in addition to the natural amide bonds, viz. —CO—NH— bonds. Such modifications of the amino acids naturally occurring in peptides are within the scope of the present invention.

Peptide compounds which, according to the invention, are labelled with a metal isotope as indicated above, are provided, directly or through a spacing group, with a chelating group, said chelating group being attached by an amide bond to an amino group of said peptide compound. Said chelating group is preferably derived from ethylene diamine tetra-acetic acid (EDTA), diethylene triamine penta-acetic acid (DTPA), cyclohexyl 1,2-diamine tetra-acetic acid (CDTA), ethyleneglycol-0,0'-bis(2-aminoethyl)-N,N,N',N'-tetra-acetic acid (EGTA), N,N-bis(hydroxybenzyl)-ethylenediamine-N,N'-diacetic acid (HBED), triethylene tetramine hexa-acetic acid (TTHA), 1,4,7,10-tetraazacyclododecane-N,N'-,N'',N'''-tetra-acetic acid (DOTA), hydroxyethyldiamine triacetic acid (HEDTA), 1,4,8,11-tetra-azacyclotetradecane-N,N',N'',N'''-tetra-acetic acid (TETA), substituted DTPA, substituted EDTA, or from a compound of the general formula

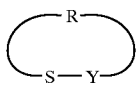
(III)

wherein R is a branched or non-branched, optionally substituted hydrocarbyl radical, which may be interrupted by one or more heteroatoms selected from N, O and S and/or by one or more NH groups, and Y is a group which is capable of reacting with an amino group of the peptide and which is preferably selected from the group consisting of carbonyl, carbimidoyl, N—($C_1$–$C_6$)alkylcarbimidoyl, N-hydroxycarbimidoyl and N—($C_1$–$C_6$)alkoxycarbimidoyl.

Examples of suitable chelators of the general formula III are unsubstituted or substituted 2-iminothiolanes and 2-iminothiacyclohexanes, in particular 2-imino-4-mercaptomethylthiolane. Said optionally present spacing group has preferably the general formula

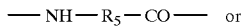
(IV)

or

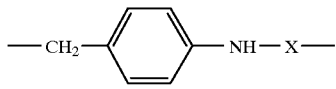
(V)

wherein $R_5$ is a $C_1$–$C_{10}$ alkylene group, a $C_1$–$C_{10}$ alkylidene group or a $C2$–$C_{10}$ alkenylene group, and X is a thiocarbonyl group or a methylcarbonyl group.

In connection with their biological properties, in particular their binding affinity to neurotensin receptors and their in vivo stability, and with their synthetic accessibility, the following labelled peptide compounds according to the invention are preferred:

(1) (2-*I-phenyl)acetyl-$^1$Arg-$^2$Arg-$^3$Pro-$^4$Tyr-$^5$Ile-$^6$Leu-OH (SEQ ID NO:4)
(2) (4*I-phenyl)acetyl-$^1$Arg-$^2$Arg-$^3$Pro-$^4$Tyr-$^5$-Ile-$^6$Leu-OH (SEQ ID NO:4)
(3) 2-*I-benzoyl-$^1$Arg-$^2$Arg-$^3$Pro-$^4$Tyr-$^5$Ile-$^6$Leu-OH (SEQ ID NO:4)
(4) 4-*I-benzoyl-$^1$Arg-$^2$Arg-$^3$Pro-$^4$Tyr-$^5$Ile-$^6$Leu-OH (SEQ ID NO:4)
(5) (4-F-2-*I-phenyl)acetyl-$^1$Arg-$^2$Arg-$^3$Pro-$^4$Tyr-$^5$Ile-$^6$Leu-OH (SEQ ID NO:4)
(6) (4-F-2-*I-benzoyl)-$^1$Arg-$^2$Arg-$^3$Pro-$^4$Tyr-$^5$Ile-$^6$Leu-OH (SEQ ID NO:4) as well as variants of compounds (1) to (6), wherein $^1$Arg is attached to $^2$Arg by pseudo peptide bonds,
(7) (2-*I-phenyl)acetyl-$^1$Lys-$^2$Arg-$^3$Pro-$^4$Tyr-$^5$Ile-$^6$Leu-OH (SEQ ID NO:5)
(8) (2-*I-phenyl)acetyl-$^1$Arg-$^2$Lys-$^3$Pro-$^4$Tyr-$^5$Ile-$^6$Leu-OH (SEQ ID NO:6)
(9) Ac-$^1$Arg-$^2$Arg-$^3$Pro-$^4$[(2-*I-Tyr]-$^5$Ile-$^6$Leu-OH (SEQ ID NO:4)
(10) Ac-$^1$Arg-$^2$Arg-$^3$Pro-$^4$[2-*I-Trp]-$^5$Ile-$^6$Leu-OH (SEQ ID NO:7)
(11) Ac-$^1$Arg-$^2$Arg-$^3$Pro-$^4$[5-*I-Trp]-$^5$Ile-$^6$Leu-OH (SEQ ID NO:7)
(12) Ac-$^1$Arg-$^2$Arg-$^3$Pro-$^4$[7-*I-Trp]-$^5$Ile-$^6$Leu-OH (SEQ ID NO:7)
(13) [*M-DTPA]-$^1$Arg-$^2$Arg-$^3$Pro-$^4$Tyr-$^5$Ile-$^6$Leu-OH (SEQ ID NO:4)
(14) [*M-EDTA]-$^1$Arg-$^2$Arg-$^3$Pro-$^4$Tyr-$^5$Ile-$^6$Leu-OH (SEQ ID NO:4)
(15) [*M-(2-iminothiolanes)]-$^1$Arg-$^2$Arg-$^3$Pro-$^4$Tyr-$^5$Ile-$^6$Leu-OH (SEQ ID NO:4)
(16) [*M-(4-mercaptomethyl-2-iminothiolane)]-$^1$Arg-$^2$Arg-$^3$Pro-$^4$-Tyr-$^5$Ile-$^6$Leu-OH (SEQ ID NO:4);

wherein *I is $I^{123}$, $^{125}I$ or $^{131}I$, and *M is $^{111}$In, $^{99m}$Tc, $^{186}$Re, $^{166}$Ho, $^{153}$Sm or $^{161}$Tb.

The above labelled peptide compounds have been tested in a number of suitable model experiments that are predictive for in vivo application. These experiments are described in the Examples. From the results of these experiments it will be evident, that the labelled peptide compounds of the present invention have properties which make them suitable for diagnostic and therapeutic purposes. If labelled with a suitable isotope for diagnostic purposes, the peptide compound remains sufficiently long intact after administration to permit imaging of the target organ or tissue without presenting a disturbing background, for example, due to detached label. If labelled with a suitable radioisotope for therapy, such-labelled peptides are promising therapeutic agents for the treatment of a number of malignant tumours that are related to neurotensin binding places, such as small cell lung carcinoma, colon carcinoma and meningiomas.

The new radiohalogenated peptide compounds of the invention can be prepared in a manner known per se for related compounds. So the invention also relates to a method of preparing a radiohalogenated peptide compound as defined hereinbefore, characterized in that a compound of the general formula

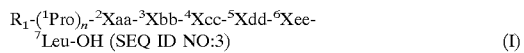
(I)

wherein Xaa, Xbb, Xcc, Xdd, Xee, n and $R_1$ have the meanings given above, and which compound is substituted with a non-radioactive bromine or iodine atom, attached to $^4$Tyr in the 2-position of the phenyl ring, to $^4$Trp, or to the aryl group of substituent $R_1$;
is reacted with a water-soluble halogenide, selected from $^{123}I^-$, $^{124}I^-$, $^{125}I^-$, $^{131}I^-$, $^{75}Br^-$$^{76}Br^-$, $^{77}Br^-$ and $^{82}Br^-$, in the presence of copper(I) ions, a water-soluble acid and a reducing agent.

Such a halogen exchange reaction is described in European patent no. 165630. An example of a suitable water-soluble acid is citric acid; examples of suitable reducing agents are Sn(II) salts, gentisic acid, isoascorbic acid, a monosaccharide and a sulphite.

The new metal-labelled peptide compounds of the invention can also be prepared in a manner known per se for related compounds. For this purpose the peptide molecule is derivatized with the desired chelating agent as defined hereinbefore, e.g. EDTA, DTPA, etc., directly or after introduction of a spacing group as defined above, after which the compound obtained, having the general formula

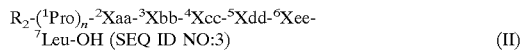
(II)

wherein:
Xaa, Xbb, Xcc, Xdd, Xee and n have the meanings given above, and $R_2$ is a chelating group attached by an amide bond or through a spacing group to the peptide molecule;
is reacted with a metal isotope, as defined hereinbefore, in the form of a salt or of a chelate bonded to a comparatively weak chelator, in order to form a complex.

Suitable examples of salts or chelates of the desired metal isotope are: $^{111}$In-oxinate, $^{99m}$Tc-tartrate, etc. The complex-forming reaction can generally be carried out in a simple manner and under conditions that are not detrimental to the peptide.

The invention further relates to a pharmaceutical composition, comprising in addition to a pharmaceutically acceptable carrier material and, if desired, at least one pharmaceutically acceptable adjuvant, as the active substance a labelled peptide compound as defined hereinbefore.

The invention also relates to a method for detecting and locating tissues having neurotensin receptors in the body of a warm-blooded living being, which comprises (i) administering to said being a composition comprising, in a quantity sufficient for external imaging, a labelled peptide compound as defined hereinbefore, wherein said peptide is labelled with (a) a metal isotope selected from the group consisting of $^{99m}$Tc, $^{203}$Pb, $^{67}$Ga, $^{68}$Ga, $^{72}$As, $^{111}$In, $^{113m}$In, $^{97}$Ru, $^{62}$Cu, $^{64}$Cu, $^{52}$Fe, $^{52}$Mn, $^{51}$Cr, or (b) with a radioactive halogen isotope, selected from $^{123}$I, $^{131}$I, $^{75}$Br, $^{76}$Br and $^{77}$Br, and thereupon (ii) subjecting said being to external imaging to determine the targeted sites in the body of said being in relation to the background activity.

The invention also relates to a method of intraoperatively detecting and locating tissues having neurotensin receptors in the body of a warm-blooded living being, which comprises (1) administering to said being a composition comprising, in a quantity sufficient for detection by a gamma detecting probe, a peptide compound as defined above, labelled with a radioisotope, selected from $^{161}$Tb, $^{123}$I and $^{125}$I, preferably $^{161}$Tb or $^{125}$I, and thereupon (ii), after allowing the active substance to be taken up in said tissues and after blood clearance of radioactivity, subjecting said being to a radioimmunodetection technique in the relevant area of the body of said being, by using a gamma detecting probe.

The above radioisotope, viz. in particular $^{161}$Tb or $^{125}$I, allows the use of a such-labelled peptide compound in the technique of radioguided surgery, wherein relevant tissues in the body of a patient can be detected and located intraoperatively by means of a gamma detecting probe. The surgeon can, intraoperatively, use this probe to find the lesions in which uptake of the compound labelled with said radioisotope, which is a low-energy gamma photon emittor, has taken place.

As mentioned hereinbefore, it is known from literature that certain tumour cells, such as small cell lung carcinoma, colon carcinoma and meningiomas, have neurotensin receptors on their surface. Therefore, the peptide compounds of the present invention, provided they are radiolabelled with isotopes suitable for the purpose, can be used for the therapeutic treatment of these tumours. So the invention further relates to a method for the therapeutic treatment of tumours, having on their surface a high density of neurotensin receptor sites, in the body of a warm-blooded living being, which comprises administering to said being a composition comprising, in a quantity effective for combating or controlling tumours, a peptide compound as defined above, said peptide compound being labelled with a metal isotope selected from the group consisting of $^{186}$Re, $^{188}$Re, $^{77}$As, $^{90}$Y, $^{67}$Cu, $^{169}$Er, $^{121}$Sn, $^{127}$Te, $^{142}$Pr, $^{143}$Pr, $^{198}$Au, $^{199}$Au, $^{161}$Tb, $^{109}$Pd, $^{165}$Dy, $^{149}$Pm, $^{151}$Pm, $^{153}$Sm, $^{157}$Gd, $^{159}$Gd, $^{166}$Ho, $^{172}$Tm, $^{169}$Yb, $^{175}$Yb, $^{177}$Lu, $^{105}$Rh and $^{111}$Ag.

In case a radioactive labelled peptide compound is used as a diagnostic agent, it is frequently impossible to put the ready-for-use composition at the disposal of the user, in connection with the often poor shelf life of the radiolabelled compound and/or the short half-life of the radionuclide used. In such cases the user will carry out the labelling reaction with the radionuclide in the clinical hospital or laboratory. For this purpose the various reaction ingredients are then offered to the user in the form of a so-called "kit". It will be obvious that the manipulations necessary to perform the desired reaction should be as simple as possible to enable the user to prepare from the kit the radioactive labelled composition by using the facilities that are at his disposal. Therefore the invention also relates to a kit for preparing a radiopharmaceutical composition.

Such a kit according to the present invention may comprise (i) a peptide compound having a selective affinity to neurotensin receptors and having the general formula II as presented hereinbefore, to which substance, if desired, an inert pharmaceutically acceptable carrier and/or formulating agents and/or adjuvants is/are added, (ii) a solution of a salt or chelate of a suitable radionuclide, and (iii) instructions for use with a prescription for reacting the ingredients present in the kit.

Suitable radionuclides for the above kit are the following metal isotopes: $^{203}$Pb, $^{67}$Ga, $^{68}$Ga, $^{72}$As, $^{111}$In, $^{113m}$In, $^{97}$Ru, $^{62}$Cu, $^{99m}$Tc, $^{186}$Re, $^{188}$Re, $^{64}$Cu, $^{52}$Fe, $^{52m}$Mn, $^{51}$Cr, $^{77}$As, $^{90}$Y, $^{67}$Cu, $^{169}$Er, $^{121}$Sn, $^{127}$Te, $^{142}$Pr, $^{143}$Pr, $^{198}$Au, $^{199}$Au, $^{161}$Tb, $^{109}$Pd, $^{165}$Dy, $^{149}$Pm, $^{151}$Pm, $^{153}$Sm, $^{157}$Gd, $^{159}$Gd, $^{166}$Ho, $^{172}$Tm, $^{169}$Yb, $^{175}$Yb, $^{177}$Lu, $^{105}$Rh and $^{111}$Ag.

Preferably the peptide compound to be used as an ingredient of the above kit has been modified by a reaction with a chelating agent as defined hereinbefore. The resulting peptide conjugate provides a facility for firmly attaching the radionuclide in a simple manner. Suitable chelating agents for modifying the peptide are described in detail hereinbefore. N-containing di- or polyacetic acids or their derivatives, such as the compounds mentioned before, have proved to be pre-eminently suitable for attaching various metal radionuclides, such as In-111 and In-113m, to the peptide molecules. The kit to be supplied to the user may also comprise the ingredient(s) defined sub (i) above, together with instructions for use, whereas the solution of a salt or chelate of the radionuclide, defined sub (ii) above, which solution has a limited shelf life, may be put to the disposal of the user separately.

In case the kit serves to prepare a radiopharmaceutical composition labelled with Tc-99m, Re-186 or Re-188, such a kit according to the present invention may comprise, in addition to the ingredient(s) defined sub (i) above, (ii) a reducing agent and, if desired, a chelator, and (iii) instructions for use with a prescription for reacting the ingredients of the kit with Tc-99m in the form of a pertechnetate solution, or with Re-186 or Re-188 in the form of a perrhenate solution. If desired, the ingredients of the kit may be combined, provided they are compatible. The kit should comprise a reducing agent to reduce the pertechnetate or perrhenate, for example, a dithionite, a metallic reducing agent or a complex-stabilizing reducing agent, e.g. $SnCl_2$, Sn(II)-tartrate, Sn(II)-phosphonate or -pyrophosphate, or Sn(II)-glucoheptonate. The pertechnetate or perrhenate solution can simply be obtained by the user from a suitable generator.

In a preferred embodiment the kit according to the present invention comprises a modified peptide or a peptide conjugate, obtained by modifying the peptide as defined hereinbefore by a treatment with a chelating agent. Suitable chelating agents have been described hereinbefore.

When the radionuclide is present in the kit itself, the complex forming reaction with the peptide conjugate can simply be produced by combining the components in a neutral medium and causing them to react. For that purpose the radionuclide may be presented to the peptide conjugate in the form of a chelate bonded to a comparatively weak chelator, as described hereinbefore.

When the kit comprises a peptide conjugate as defined hereinbefore and is intended for the preparation of a radiopharmaceutical composition, labelled with Tc-99m, Re-186 or Re-188, the radionuclide will preferably be added separately in the form of a pertechnetate or perrhenate solution. In that case the kit will comprise a suitable reducing agent and, if desired, a chelator, the former to reduce the pertechnetate or the perrhenate. As a reducing agent may be used, for example, a dithionite or a metallic reducing agent. The ingredients may optionally be combined, provided they are compatible. Such a monocomponent kit, in which the combined ingredients are preferably lyophilized, is excellently suitable for being reacted, by the user, with the radionuclide solution. As a reducing agent for the above-mentioned kits is preferably used a metallic reducing agent, for example, Sn(II), Ce(III), Fe(II), Cu(I), Ti(III) or Sb(III); Sn(II) is excellently suitable. The peptide constituent of the above-mentioned kits, i.e. preferably the peptide conjugate, may be supplied as a solution, for example, in the form of a physiological saline solution, or in some buffer solution, but is preferably present in a dry condition, for example, in the lyophilized condition. When used as a component for an injection liquid it should be sterile, in which, when the constituent is in the dry state, the user should preferably use a sterile physiological saline solution as a solvent. If desired, the above-mentioned constituent may be stabilized in the conventional manner with suitable stabilizers, for example, ascorbic acid, gentisic acid or salts of these acids, or it may comprise other auxiliary agents, for example, fillers, such as glucose, lactose, mannitol, and the like.

The invention will now be described in greater detail with reference to the following specific Examples.

EXAMPLE I

Synthesis of Radiolabelled Peptide Compounds (1), (2), (3) and (4)

(a) Synthesis of the Corresponding Bromo-substituted Peptide Compounds

The starting bromo-substituted peptides, viz. bromo-substituted benzoyl-Arg-Arg-Pro-Tyr-Ile-Leu-OH (SEQ ID NO:4) and phenylacetyl-Arg-Arg-Pro-Tyr-Ile-Leu-O-H (SEQ ID NO:4), are synthesized by using the solid phase peptide synthesis (SPPS) methodology, employing N-α-tert.-butyloxycarbonyl (Boc) protected amino acids. During this synthesis the side chain of Arg is protected with a tosyl (Tos) group, the phenolic side chain of tyrosine with o-bromo-benzyloxycarbonyl (o-Br—Z) group.

The first amino acid is attached to a resin (chloromethylpolystyrene, crosslinked with 1% of 1,4-divinylbenzene) via a Cs-salt of the desired amino acid, i.c. leucine. The substitution grade (0.60 mmol/g resin) is determined via the picric acid method.

The peptide is assembled using a repetitive cycle, as follows:
- deprotection of the main-chain protecting group, i.e. the Boc group, with a trifluoroacetic acid (TFA) solution (TFA/dichloromethane/anisole, 49/49/2);
- neutralisation of the TFA salt with diisopropylethylamine (DIEA);
- coupling of the free amine with the carboxylic function of the next amino acid; N,N'-dicyclohexylcarbodiimide (DCC) and 1-hydroxybenzotriazole (HOBt) are used as coupling agents.

This cycle is repeated until the peptide chain is assembled. The peptide is cleaved from the resin by reaction with liquid HP. Acetic acid extraction is used to separate the peptide from the resin. After lyophilization, the crude peptide is purified by RP-HPLC, using acetonitrile/$H_2O$/TFA-x/(100-x)/0. 00with a gradient of x=15%→40% (0–20 min.) and a Vydac® RP—$C_{18}$ column.

Finally the purity of the peptide is verified by analytical RP-HPLC and thin layer chromatography. The peptide is characterized by FAB mass spectrometry. The four bromo-substituted peptide compounds are obtained in yields varying between 31 and 61%.

(b) Radioiodination with $^{131}$I.

The peptides are radioiodinated by nucleophilic displacement of bromine by iodine-131, according to the procedure as described in European patent no. 165630. In a typical example:

stock solution: 1 mg $SnSO_4$, 25 mg 2,5-dihydroxybenzoic acid (gentisic acid), 35 mg citric acid monohydrate, in 2.5 ml 10% AcOH.aq (v/v);

$Cu^{2-}$-solution: 32.5 mg $CuSO_4.5H_2O$ in 10 ml water (0.013 M). The peptide (1 mg) is dissolved in 500 μl of stock solution and 60 μl of $Cu^{2+}$-solution. The solution is sonicated until all solutes are dissolved.

The clear solution is flushed with $N_2$ for 5 min. After the addition of 10 μl $Na^{131}I$ (132 μCi), the reaction mixture is heated at 140° C. for 1 hour. The mixture is finally cooled to ambient temperature. RP—HPLC is carried out to calculate the iodination yield: acetonitrile/$H_2O$/TFA-x/(100-x)/ 0.001 with a gradient of x=15%→40% (0–20 min.); Lichrospher® 100 RP-18 (5 μm) column; flow-rate 1 ml/min. The desired radioiodinated peptides (1), (2), (3) and (4) are obtained in yields of 84%, 54%, 86% and 55%, respectively (not optimized).

EXAMPLE II

Biological Experiments

Binding Assay Experiment

Binding assays are performed by studying the inhibition of [$^3$H]neurotensin binding to guinea pig forebrain membranes. The following results are obtained, using the unlabelled acetyl compound Ac-Arg-Arg-Pro-Tyr-Ile-Leu-OH (SEQ ID NO:4) (a) as the reference.

The affinity is expressed as the $pIC_{50}$ value (i.c. the concentration of peptide analogue yielding 50% inhibition).

| peptide | $pIC_{50}$ (M) |
| --- | --- |
| (a) | 8.11 |
| (1) | 8.05 |
| (2) | 7.87 |
| (3) | 8.07 |
| (4) | 8.10 |

From the above figures it will be clear that the radioiodinated analogues (1) through (4) show affinities to neurotensin receptor sites in this binding assay which are comparable with that of the unlabelled compound.

Enzymatic Stability

The enzymatic stability of the four radioiodinated analogues (1), (2), (3) and (4) is determined in vitro in human serum in a conventional manner, showing that this stability is sufficient.

Structure-activity studies of neurotensin and its analogues reveals that the same relationship, viz. structure to activity, exists in rat brain receptors as in tumour receptors. This indicates that the receptors in rat brain are the same as those in tumour cells. Therefore the above experiments show, that the tested compounds are promising tools in diagnosing malignancies related to neurotensin receptors.

We claim:
1. A labelled peptide compound, wherein the peptide selectively binds to neurotensin receptors and is represented by the general formula

$$R_1\text{-}(^1Pro)_n\text{-}^2Xaa\text{-}^3Xbb\text{-}^4Xcc\text{-}^5Xdd\text{-}^6Xee\text{-}^7Leu\text{-}OH \text{ (SEQ ID NO:2)} \quad (I)$$

wherein:

$R_1$ is a ($C_1$–$C_3$)alkanoyl group, an arylcarbonyl group, an aryl-($C_1$–$C_3$)alkanoyl group, or a chelating group attached by an amide bond or through a spacing group to the peptide molecule;

Xaa and Xbb are each individually Arg or Lys;

Xcc is an unsubstituted or substituted cyclic amino acid, preferably selected from Pro and Hyp;

Xdd is Tyr, Trp or Phe;

Xee is Leu, Ile or tert-butylalanine; and n is 0 or 1;

and wherein said peptide is labelled with (a) a metal isotope selected from the group consisting of $^{99m}Tc$, $^{203}Pb$, $^{67}Ga$, $^{68}Ga$, $^{72}As$, $^{111}In$, $^{113m}In$, $^{97}Ru$, $^{62}Cu$, $^{64}Cu$, $^{52}Fe$, $^{52m}Mn$, $^{51}Cr$, $^{186}Re$, $^{188}Re$, $^{77}As$, $^{90}Y$, $^{67}Cu$, $^{169}Er$, $^{121}Sn$, $^{127}Te$, $^{142}Pr$, $^{143}Pr$, $^{198}Au$, $^{199}Au$, $^{161}Tb$, $^{109}Pd$, $^{165}Dy$, $^{149}Pm$, $^{151}Pm$, $^{153}Sm$, $^{157}Gd$, $^{159}Gd$, $^{166}Ho$, $^{172}Tm$, $^{169}Yb$, $^{175}Yb$, $^{177}Lu$, $^{105}Rh$ and $^{111}Ag$, or (b) with a radioactive halogen isotope; with the provise that:

(i) if the label is a metal isotope, $R_1$ represents a chelating group for chelating said isotope; and (ii) if the label is a radioactive halogen isotope, said halogen isotope is attached to $^4Tyr$ in the 2-position of the phenyl ring, to $^4Trp$, or to the aryl group of substituent $R_1$.

2. A labelled peptide compound as claimed in claim 1, wherein said peptide is labelled with a radioactive halogen isotope selected from the group consisting of $^{123}I$, $^{124}I$, $^{125}I$, $^{131}I$, $^{75}Br$, $^{76}Br$, $^{77}Br$ and $^{82}Br$.

3. A labelled peptide compound as claimed in claim 1, wherein said peptide is labelled with a metal isotope, chelated by a chelating group $R_1$ derived from ethylene diamine tetra-acetic acid (EDTA), diethylene triamine penta-acetic acid (DTPA), cyclohexyl 1,2-diamine tetra-acetic acid (CDTA), ethyleneglycol-0,0'-bis(2-aminoethyl)-N,N,N',N'-tetra-acetic acid (EGTA), N,N-bis(hydroxybenzyl)-ethylenediamine-N,N'-diacetic acid (HBED), triethylene tetramine hexa-acetic acid (TTHA), 1,4,7,10-tetraazacyclododecane-N,N',N",N'"-tetra-acetic acid (DOTA), hydroxyethyldiamine triacetic acid (HEDTA), 1,4,8,11-tetra-azacyclo-tetradecane-N,N', N",N'"-tetra-acetic acid (TETA), substituted DTPA, substituted EDTA, or from a compound of the general formula

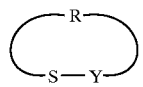

(III)

wherein R is a branched or non-branched, optionally substituted hydrocarbyl radical, which may be interrupted by one or more hetero-atoms selected from N, O and S and/or by one or more NH groups, and Y is a group which is capable of reacting with an amino group of the peptide and which is preferably selected from the group
consisting of carbonyl, carbimidoyl, N-($C_1$–$C_6$) alkylcarbimidoyl, N-hydroxycarbimidoyl and N-($C_1$–$C_6$)alkoxycarbimidoyl;

and wherein said optionally present spacing group has the general formula

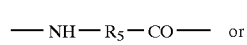 (IV)

or

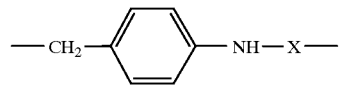 (V)

wherein $R_5$ is a $C_1$–$C_{10}$ alkylene group, a $C_1$–$C_{10}$ alkylidene group or a $C_2$–$C_{10}$ alkenylene group, and X is a thiocarbonyl group or a methylcarbonyl group.

4. A method of preparing a radiohalogenated peptide compound as claimed in claim 2, characterized in that a compound of the general formula $$R_1\text{-}(^1Pro)_n\text{-}^2Xaa\text{-}^3Xbb\text{-}^4XCC\text{-}^5xdd\text{-}^6Xee\text{-}^7Leu\text{-}OH \text{ (SEQ ID NO:2)} \quad (I)$$

wherein Xaa, Xbb, Xcc, Xdd, Xee, n and $R_1$ have the meanings given in claim 1, and which compound is substituted with a non-radioactive bromine or iodine atom, attached to $^4Tyr$ in the 2-position of the phenyl ring, to $^4Trp$, or to the aryl group of substituent $R_1$;

is reacted with a water-soluble halogenide, selected from $^{123}I^-$, $^{124}I^-$, $^{125}I^-$, $^{131}I^-$, $^{75}Br^-$, $^{76}Br^-$, $^{77}Br^-$ and $^{82}Br^-$, in the presence of copper(I) ions, a water-soluble acid and a reducing agent.

5. A method of preparing a metal-labelled peptide compound as claimed in claim 3, characterized in that a compound of the general formula $$R_2\text{-}(^1Pro)_n\text{-}^2Xaa\text{-}^3Xbb\text{-}^4Xcc\text{-}^5Xdd\text{-}^6Xee\text{-}$$

$^7$Leu-OH (SEQ ID NO:3)        (II)

wherein:

Xaa, Xbb, Xcc, Xdd, Xee and n have the meaning given in claim 1, and R$_2$ is a chelating group attached by an amide bond or through a spacing group to the peptide molecule;

is reacted with a metal isotope as defined in claim 1 in the form of a salt or of a chelate bonded to a comparatively weak chelator, in order to form a complex.

6. A pharmaceutical composition, comprising in addition to a pharmaceutically acceptable carrier material and, optionally, at least one pharmaceutically acceptable adjuvant, as the active substance a labelled peptide compound as claimed in claim 1, 2 or 3.

7. A method for detecting and locating tissues having neurotensin receptors in the body of a warm-blooded living being, which comprises (i) administering to said being a composition comprising, in a quantity sufficient for external imaging, a labelled peptide compound as claimed in claim 1, 2 or 3, wherein said peptide is labelled with (a) a metal isotope selected from the group consisting of $^{99m}$Tc, $^{203}$Pb, $^{67}$Ga, $^{68}$Ga, $^{72}$As, $^{111}$In, $^{113m}$In, $^{97}$Ru, $^{62}$Cu, $^{64}$Cu, $^{52}$Fe, $^{52m}$Mn, $^{51}$Cr, or (b) with a radioactive halogen isotope, selected from $^{123}$I, $^{131}$I, $^{75}$Br, $^{76}$Br and $^{77}$Br, and thereupon (ii) subjecting said being to external imaging to determine the targeted sites in the body of said being in relation to the background activity.

8. A method of intraoperatively detecting and locating tissues having neurotensin receptors in the body of a warm-blooded living being, which comprises (1) administering to said being a composition comprising, in a quantity sufficient for detection by a gamma detecting probe, a labelled peptide compound as claimed in claim 1, wherein the radioisotope is $^{161}$Tb, $^{123}$I or $^{125}$I, preferably $^{161}$Tb or $^{125}$I, and thereupon (ii), after allowing the active substance to be taken up in said tissues and after blood clearance of radioactivity, subjecting said being to a radioimmunodetection technique in the relevant area of the body of said being, by using a gamma detecting probe.

9. A kit for preparing a radiopharmaceutical composition, comprising (i) a peptide compound which selectively binds to neurotensin receptors and having the general formula II, to which compound, if desired, an inert pharmaceutically acceptable carrier and/or formulating agents and/or adjuvants is/are added, (ii) a solution of a salt or chelate of a metal isotope selected from the group consisting of $^{203}$Pb, $^{67}$Ga, $^{68}$Ga, $^{72}$As, $^{111}$In, $^{113m}$In, $^{97}$Ru, $^{62}$Cu, $^{99m}$Tc, $^{186}$Re, $^{188}$Re, $^{64}$Cu, $^{52}$Fe, $^{52m}$Mn, $^{51}$Cr, $^{77}$As, $^{90}$Y, $^{67}$Cu, $^{169}$Er, $^{121}$Sn, $^{127}$Te, $^{142}$Pr, $^{143}$Pr, $^{198}$Au, $^{199}$Au, $^{161}$Tb, $^{109}$Pd, $^{165}$Dy, $^{149}$Pm, $^{151}$Pm, $^{153}$Sm, $^{157}$Gd, $^{159}$Gd, $^{166}$Ho, $^{172}$Tm, $^{169}$Yb, $^{175}$Yb, $^{177}$Lu, $^{105}$Rh and $^{111}$Ag, and (iii) instructions for use with a prescription for reacting the ingredients present in the kit.

10. A kit for preparing a radiopharmaceutical composition, comprising (i) a peptide compound which selectively binds to neurotensin receptors and having the general formula II, to which compound, if desired, an inert pharmaceutically acceptable carrier and/or formulating agents and/or adjuvants is/are added, (ii) a reducing agent, and, if desired, a chelator, said ingredients (i) and (ii) optionally being combined, and (iii) instructions for use with a prescription for reacting the ingredients of the kit with $^{99m}$Tc in the form of a pertechnetate solution or with $^{186}$Re or $^{188}$Re in the form of a perrhenate solution.

* * * * *

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
        (A) LENGTH: 13 amino acids
        (B) TYPE: amino acid
        (C) STRANDEDNESS: Not Relevant
        (D) TOPOLOGY: Not Relevant (ii) MOLECULE TYPE: peptide (v) FRAGMENT TYPE: internal (ix) FEATURE:
        (A) NAME/KEY: Modified-site
        (B) LOCATION: 1
        (D) OTHER INFORMATION: /product= "PYROGLUTAMIC ACID"

(xi) SEQUENCE DESCRIPTION: SEQ ID NO:1:

```
Glu Leu Tyr Glu Asn Lys Pro Arg Arg Pro Tyr Ile Leu
1               5                   10
```

(2) INFORMATION FOR SEQ ID NO:2:

(i) SEQUENCE CHARACTERISTICS:
        (A) LENGTH: 7 amino acids
        (B) TYPE: amino acid
        (C) STRANDEDNESS: Not Relevant
        (D) TOPOLOGY: Not Relevant (ii) MOLECULE TYPE: peptide (v) FRAGMENT TYPE: internal (ix) FEATURE:
        (A) NAME/KEY: Modified-site
        (B) LOCATION: 1
        (D) OTHER INFORMATION: /product= "Pro may be absent; N-
           terminal residue is substituted with a C1-C3 alkanoyl,
           arylcarbonyl, aryl(C1-C3)alkanoyl or chelating group"

(ix) FEATURE:
        (A) NAME/KEY: Modified-site
        (B) LOCATION: 2
        (D) OTHER INFORMATION: /product= "Xaa is Arg or
           Lys"

(ix) FEATURE:
        (A) NAME/KEY: Modified-site
        (B) LOCATION: 3
        (D) OTHER INFORMATION: /product= "Xaa is Arg or
           Lys"

(ix) FEATURE:
        (A) NAME/KEY: Modified-site
        (B) LOCATION: 4
        (D) OTHER INFORMATION: /product= "Xaa is a subtituted
           or unsubstituted cyclic amino acid"

(ix) FEATURE:
        (A) NAME/KEY: Modified-site
        (B) LOCATION: 5
        (D) OTHER INFORMATION: /product= "Xaa is Tyr, Trp or
           Phe"

(ix) FEATURE:
        (A) NAME/KEY: Modified-site
        (B) LOCATION: 6
        (D) OTHER INFORMATION: /product= "Xaa is Leu, Ile or
           tert-butylalanine"

(xi) SEQUENCE DESCRIPTION: SEQ ID NO:2:

Pro Xaa Xaa Xaa Xaa Xaa Leu
1               5

(2) INFORMATION FOR SEQ ID NO:3:

(i) SEQUENCE CHARACTERISTICS:
        (A) LENGTH: 7 amino acids
        (B) TYPE: amino acid
        (C) STRANDEDNESS: Not Relevant
        (D) TOPOLOGY: Not Relevant (ii) MOLECULE TYPE: peptide (v) FRAGMENT TYPE: internal (ix) FEATURE:
        (A) NAME/KEY: Modified-site
        (B) LOCATION: 1
        (D) OTHER INFORMATION: /product= "Pro may be absent; N-
            terminal residue is substituted with a chelating group"

(ix) FEATURE:
        (A) NAME/KEY: Modified-site
        (B) LOCATION: 2
        (D) OTHER INFORMATION: /product= "Xaa is Arg or
            Lys"

(ix) FEATURE:
        (A) NAME/KEY: Modified-site
        (B) LOCATION: 3
        (D) OTHER INFORMATION: /product= "Xaa is Arg or
            Lys"

(ix) FEATURE:
        (A) NAME/KEY: Modified-site
        (B) LOCATION: 4
        (D) OTHER INFORMATION: /product= "Xaa is a subtituted
            or unsubstituted cyclic amino acid"

(ix) FEATURE:
        (A) NAME/KEY: Modified-site
        (B) LOCATION: 5
        (D) OTHER INFORMATION: /product= "Xaa is Tyr, Trp or
            Phe"

(ix) FEATURE:
        (A) NAME/KEY: Modified-site
        (B) LOCATION: 6
        (D) OTHER INFORMATION: /product= "Xaa is Leu, Ile or
            tert-butylalanine"

(xi) SEQUENCE DESCRIPTION: SEQ ID NO:3:

Pro Xaa Xaa Xaa Xaa Xaa Leu
1               5

(2) INFORMATION FOR SEQ ID NO:4:

(i) SEQUENCE CHARACTERISTICS:
        (A) LENGTH: 6 amino acids
        (B) TYPE: amino acid
        (C) STRANDEDNESS: Not Relevant
        (D) TOPOLOGY: Not Relevant (ii) MOLECULE TYPE: peptide (v) FRAGMENT TYPE: internal (ix) FEATURE:
        (A) NAME/KEY: Modified-site
        (B) LOCATION: 1
        (D) OTHER INFORMATION: /product= "N-substituted with
            (2-I-phenyl)acetyl, (4-I-phenyl)acetyl, 2-I-benzoyl, 4-I-
            benzoyl, (4-F-2-I-phenyl)acetyl, (4-F-2-I-benzoyl),
            acetyl, M-DTPA, M-EDTA, M-(2-iminothiolane) or M-
            (4-mercaptomethyl-2-iminothiolane), wherein I is 123-I, 125-I or 131-I and M is 111-In, 99m-Tc, 186-Re, 166-Ho, 153-Sm or 161-Tb"

(ix) FEATURE:
        (A) NAME/KEY: Modified-site
        (B) LOCATION: 4
        (D) OTHER INFORMATION: /product= "may be 2-I-Tyr,
            wherein I is 123-I, 125-I or 131-I"

(xi) SEQUENCE DESCRIPTION: SEQ ID NO:4:

Arg Arg Pro Tyr Ile Leu
1               5

(2) INFORMATION FOR SEQ ID NO:5:

(i) SEQUENCE CHARACTERISTICS:
        (A) LENGTH: 6 amino acids
        (B) TYPE: amino acid
        (C) STRANDEDNESS: Not Relevant
        (D) TOPOLOGY: Not Relevant (ii) MOLECULE TYPE: peptide (v) FRAGMENT TYPE: internal (ix) FEATURE:
        (A) NAME/KEY: Modified-site
        (B) LOCATION: 1
        (D) OTHER INFORMATION: /product= "(2-I-phenyl)acetyl
            lysine, wherein I is 123-I, 125-I or 131-I"

(xi) SEQUENCE DESCRIPTION: SEQ ID NO:5:

Lys Arg Pro Tyr Ile Leu
1               5

(2) INFORMATION FOR SEQ ID NO:6:

(i) SEQUENCE CHARACTERISTICS:
        (A) LENGTH: 6 amino acids
        (B) TYPE: amino acid
        (C) STRANDEDNESS: Not Relevant
        (D) TOPOLOGY: Not Relevant (ii) MOLECULE TYPE: peptide (v) FRAGMENT TYPE: internal (ix) FEATURE:
        (A) NAME/KEY: Modified-site
        (B) LOCATION: 1
        (D) OTHER INFORMATION: /product= "(2-I-phenyl)acetyl
            arginine, wherein I is 123-I, 125-I or 131-I"

(xi) SEQUENCE DESCRIPTION: SEQ ID NO:6:

Arg Lys Pro Tyr Ile Leu
1               5

(2) INFORMATION FOR SEQ ID NO:7:

(i) SEQUENCE CHARACTERISTICS:
        (A) LENGTH: 6 amino acids
        (B) TYPE: amino acid
        (C) STRANDEDNESS: Not Relevant
        (D) TOPOLOGY: Not Relevant (ii) MOLECULE TYPE: peptide (v) FRAGMENT TYPE: internal (ix) FEATURE:
        (A) NAME/KEY: Modified-site
        (B) LOCATION: 1
        (D) OTHER INFORMATION: /product= "N-acetyl arginine"

(ix) FEATURE:
    (A) NAME/KEY: Modified-site
    (B) LOCATION: 4
    (D) OTHER INFORMATION: /product= "2-I-Trp, 5-I-Trp or
        7-I-Trp, wherein I is 123-I, 125-I or 131-I"

(xi) SEQUENCE DESCRIPTION: SEQ ID NO:7:

Arg Arg Pro Trp Ile Leu
1               5